United States Patent [19]

Mangold

[11] Patent Number: 5,391,482
[45] Date of Patent: Feb. 21, 1995

[54] METHOD AND DIAGNOSTIC AGENT FOR ENZYME SUBSTRATE STABILIZATION USING 1-ARYLSEMICARBAZIDES

[75] Inventor: Dieter Mangold, Maxdorf, Germany

[73] Assignee: Boehringer Mannheim GmbH, Mannheim, Germany

[21] Appl. No.: 633,213

[22] Filed: Dec. 21, 1990

[30] Foreign Application Priority Data

Dec. 21, 1989 [DE] Germany .................. 3942356

[51] Int. Cl.$^6$ .................. C12Q 1/62; C12Q 1/00; C12Q 1/54; G01N 21/75
[52] U.S. Cl. .................. 435/18; 435/10; 435/805; 436/166; 530/330; 530/331; 544/104; 544/73
[58] Field of Search .................. 435/18, 10, 14, 805, 435/4, 14; 436/166; 530/331, 330; 544/73, 104

[56] References Cited

U.S. PATENT DOCUMENTS

| | | | |
|---|---|---|---|
| 4,220,713 | 9/1980 | Rittersdorf et al. | 435/14 |
| 4,469,789 | 9/1984 | Berger et al. | 435/23 |
| 4,859,607 | 8/1989 | Lambert et al. | 436/166 |
| 4,900,822 | 2/1990 | von der Eltz et al. | 530/331 |
| 5,116,729 | 5/1992 | Ismail et al. | 435/10 |
| 5,126,329 | 6/1992 | Tani et al. | 536/17.4 |

FOREIGN PATENT DOCUMENTS 0034323 8/1981 European Pat. Off. .

*Primary Examiner*—Michael G. Wityshyn
*Assistant Examiner*—Louise D. Leary
*Attorney, Agent, or Firm*—Felfe & Lynch

[57] ABSTRACT

The present invention is concerned with the use of 1-arylsemicarbazides of the general formula:

$$Ar-NH-NH-CON_2$$

wherein Ar is an aryl radical optionally substituted by alkyl, alkoxy or halogen, for the stabilization of an enzyme substrate from which, by enzymatic hydrolysis, a leuko coloured material can be formed which, in turn, can be reacted by an oxidation agent to give a colored material. The present invention also provides a corresponding stabilizing process and a diagnostic agent containing such a stabilizer.

24 Claims, 1 Drawing Sheet

METHOD AND DIAGNOSTIC AGENT FOR ENZYME SUBSTRATE STABILIZATION USING 1-ARYLSEMICARBAZIDES

The present invention is concerned with the use of a 1-arylsemicarbazide for the stabilization of an enzyme substrate from which, by enzymatic hydrolysis, a leuko color material can be formed which, in turn, can be reacted by an oxidation agent to give a colored material.

Furthermore, the present invention is concerned with a process for the stabilization of an enzyme substrate characterized as above.

Finally, the present invention is concerned with a diagnostic agent for the colorimetric determination of an enzyme containing an enzyme substrate from which, by enzymatic hydrolysis, a leuko colored material can be formed which, in turn, can be reacted by an oxidation agent to give a colored material.

By hydrolases are understood enzymes which hydrolytically cleave bonds with the consumption of water. In clinical chemistry and in diagnosis, in recent years in particular the determination of the activity of those hydrolases has achieved importance which cleave ester and ether bonds. By way of example, there may be mentioned esterases, for example the carboxyl ester-cleaving enzymes occurring in leukocytes, or phosphatases, as alkaline or acid phosphatases which hydrolyse phosphoric acid esters. For the diagnosis of kidney diseases and of diseases of the urogenital tract, it has proved to be useful to detect leukocytes in urine on the basis of their inherent esterolytic activity. The activity determination of acid phosphatase is a valuable means for the early diagnosis of prostatic carcinoma. Alkaline phosphatase can be used as labelling enzyme for enzyme immunoassays.

Glycosidases, for example galactosidases, glucosidases, mannosidases, amylase or N-acetyl-$\beta$-D-glucosaminidase cleave glycosidic bonds. In the human and animal organism, they fulfil a plurality of physiological functions. Thus, for example, $\beta$-D-galactosidase plays an important part in carbohydrate metabolism since, due to it, the hydrolysis of lactose takes place. Furthermore, $\beta$-D-galactosidase is a key enzyme in the break down of glycolipids, mucopolysaccharides and glycoproteins. Further physiologically important glycosidases which can be mentioned include $\alpha$-D-galactosidase, $\alpha$-D- and $\beta$-D-glucosidase and $\alpha$-D-mannosidase.

Over and above their physiological value, in recent years the glycosidases have achieved importance in the diagnostic as well as in the biotechnological fields. Thus, for example, these enzymes are used to an increasing extent as indicator enzymes for enzyme immunoassays. In this connection, the use of $\beta$-D-galactosidase is to be especially mentioned.

The presence of the enzyme N-acetyl-$\beta$-D-glucosaminidase ($\beta$-NAGase) in body fluids is a valuable indicator for diseases or impaired functions in the organism. In the urine, for example, increased values in the case of kidney transplants are an indication of the rejection of a donated kidney. Increased values also occur in the case of a number of diseases and of toxic damage to the kidneys. In the saliva of women, the NAGase activity is an indication of fertility and pregnancy.

For the detection of hydrolases, these can be mixed with an appropriate substrate which is enzymatically cleaved and hereby liberates an only weakly colored or preferably colorless cleavage product which, by oxidation, can be converted into a colored material. Only weakly colored or preferably colorless cleavage products liberated from the substrate are referred to as leuko colored materials. Corresponding substrates and hydrolase determination processes are known from the prior art, for example from published European Patent Specification No. 0,274,700.

In general, the above-mentioned processes of determination can be illustrated by the following equation:

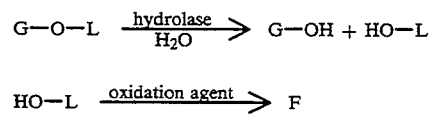

G-O-L designates the hydrolase substrate from which, by the action of an appropriate hydrolase enzyme in the presence of water, cleavage products arise. G-OH can be a corresponding acid or an alcohol, for example a sugar. HO-L is a leuko colored material which can be oxidised to give a colored material F.

As a rule, hydrolase substrates of the above-mentioned kind are more difficult to oxidise than the leuko colored materials which can be liberated therefrom by hydrolysis. This is also especially important because these hydrolase substrates are mostly used together with oxidation agents and are also often kept and stored in contact with these.

Substrates such as are mentioned hereinbefore are advantageously used where the colorimetric determination process starts from non-colored substrates and is to lead to strongly colored end products of an enzymatic cleavage. This is then, for example, the case when the substrate is used in high concentrations, for example on test strips, and/or when the highest possible sensitivity of a process of determination is to be achieved. If substrates which are themselves already colored are also used in high concentrations, then this inherent coloration can hide an only weak coloration due to the determination reaction in the case of a small enzyme concentration and thus give rise to an insensitive test. Therefore, understandably, the advantages of the colorless hydrolase substrates are only maintained as long as the substrates remain colorless even in the case of comparatively long storage and do not become colored under the storage conditions. Therefore, it must be an endeavour to store such hydrolase substrates in a form which is as stable as possible so that even comparatively long storage and/or comparatively high temperatures do not result in the formation of colorations.

Consequently, stabilizers are needed for hydrolase substrates of the described kind which a) are themselves very storage-stable and can be stored for a long time inter alia also in the case of elevated temperature without becoming colored, which b) are not oxidized by oxidation agents simultaneously present, for example iodate, and which c) do not prevent the oxidation of leuko colored material liberated from the hydrolase substrate.

From published Federal Republic of Germany Patent Specification No. 27 16 060 are known 1-arylsemicarbazides which stabilizer oxidation indicators against environmental influences, such as air and light. These oxidation indicators serve for the colorimetric detection of hydrogen peroxide. Therefore, understandably, they are not stored in the presence of strong oxidation agents. The stabilization of the oxidation indicators does not prevent the determination reaction of the indicators with the oxidation agent to be detected.

Having regard to this prior art, it was surprising to ascertain that 1-arylsemicarbazides are able to stabilise hydrolase substrates of the above-described kind which themselves are not oxidation indicators since, of course, they are not to react in the presence of strong oxidation agents but which, on the other hand, after hydrolysis by the enzyme to be determined, must, by oxidation of the corresponding leuko colored material, unimpededly show the presence of this enzyme by color formation.

The stabilization according to the present invention of hydrolase substrates from which, by enzymatic hydrolysis, a leuko colored material can be formed which, in turn, can be reacted by an oxidation agent to give a colored material, is characterized by the claims.

Thus, the subject of the present invention is the use of a 1-arylsemicarbazide of the general formula:

Ar—NH—NH—CONH$_2$   (I)

wherein Ar is an aryl radical optionally substituted by alkyl, alkoxy or halogen, for the stabilization of an enzyme substrate from which, by enzymatic hydrolysis, a leuko colored material is formed which, in turn, can be reacted by an oxidation agent to give a colored material.

A further subject of the present invention is a process for the stabilization of an enzyme substrate from which, by enzymatic hydrolysis, a leuko colored material can be formed which, in turn, can be reacted by an oxidation agent to give a colored material, wherein the substrate is brought into contact with a 1-arylsemicarbazide of the general formula:

Ar—NH—NH—CONH$_2$   (I)

in which Ar is an aryl radical optionally substituted by alkyl, alkoxy or halogen.

Finally, a subject of the present invention is a diagnostic agent for the colorimetric determination of en enzyme containing an enzyme substrate from which, by enzymatic hydrolysis, a leuko colored material can be formed which, in turn, can be reacted by an oxidation agent to give a colored material, wherein, for the stabilization of the enzyme substrate, it contains a 1-arylsemicarbazide of the general formula:

Ar—NH—NH—CONH$_2$   (I)

wherein Ar is an aryl radical optionally substituted by alkyl, alkoxy or halogen.

"Aryl" in the definition of the 1-arylsemicarbazides of general formula (I) characterises a hydrocarbon residue, preferably one with 6 to 10 ring atoms and especially the phenyl or naphthyl radical.

"Alkyl" means a straight-chained or branched alkyl radical containing up to 6 and preferably up to 4 carbon atoms. Examples thereof include the methyl, ethyl, propyl, isobutyl and tert.-butyl radicals, the methyl and ethyl radicals being preferred.

"Alkoxy" means a straight-chained or branched alkoxy radical containing up to 6 and preferably up to 4 carbon atoms. Examples thereof include the methoxy, ethoxy, propoxy, isobutoxy and tert.-butoxy radicals, the methoxy and ethoxy radicals being preferred.

"Halogen" means fluorine, chlorine, bromine or iodine and preferably chlorine.

o-Chloro-, m-chloro-, p-chloro, o-methyl-, m-methyl-, p-methyl-, o-methoxy-, m-methoxy-, p-methoxy and unsubstituted phenylsemicarbazide and naphthylsemicarbazide have proved to be especially advantageous for the use according to the present invention. Methylphenylsemicarbazides and phenylsemicarbazide have proved to be quite especially suitable, p-methylphenylsemicarbazide being especially preferred.

The 1-arylsemicarbazides used according to the present invention of general formula (I) not only increase the storage stability of hydrolase substrates of the initially described kind in absence but, in particular, also in the presence of strong oxidizing agents, for example potassium ferricyanide, perborate, peroxidase/hydrogen peroxide and preferably an iodate, for example potassium iodate.

The effect of the stabilization refers to substances present in solution and particularly in aqueous solution but especially to solid, undissolved hydrolase substrates, optionally in admixture with an oxidation agent and solid undissolved 1-arylsemicarbazide, be it, for example, crystals, powder, lyophilisate or solid materials pressed into tablet form. A stabilization in the form for the prevention of a coloration of hydrolase substrates is preferably possible in the case of test carriers in which the hydrolase substrate and the oxidation agent are present carrier-bound either together on or in an absorbent or swellable carrier material, for example paper or a polymer film, or in which the hydrolase substrate and the oxidation agent are present in or on separate carrier materials which, however, are in direct contact with one another. Examples of test carriers for the determination of hydrolases are illustrated in FIGS. 1 and 2 of the accompanying drawings.

BRIEF DESCRIPTION of DRAWINGS

FIG. 1 is a side view of a test carrier (1) for the colorimetric determination of a hydrolase enzyme. On a carrier foil (2), preferably made of a stiff synthetic material, is fixed an absorbent reagent carrier (3) by means of a covering mesh (4) which is fixed with melt adhesive (5) on to the carrier foil (2). The absorbent reagent carrier (3) can, for example, consist of paper which is impregnated with the reagents necessary for the determination, especially a hydrolase substrate, an oxidation agent and a stabilizer. The reagents can be applied to the reagent carrier (3) all at once, i.e. in one step, from a solution or they can be impregnated on in several steps by impregnation from separate solutions. Preferably, the reagent carrier (3) is first impregnated with a solution of the oxidation agent which is possibly dissolved in a buffer solution adjusted to the pH value necessary for the determination reaction, then dried and subsequently impregnated a second time with a solution which contains the hydrolase substrate and the stabilizer according to the present invention.

FIG. 2 also shows a side view of a test carrier (6) for the colorimetric determination of a hydrolase enzyme. It is constructed in a similar manner to the test carrier according to FIG. 1. However, under the covering mesh (4), which is fixed with melt adhesive (5) to a carrier foil (2), apart from an absorbent reagent carrier (3), it contains a mesh (7). This mesh, which preferably consists of a polymeric material, is impregnated with the oxidation agent. The reagent carrier (3) contains the hydrolase substrate, the stabilizer and optionally a buffer substance for the adjustment of a pH value necessary for carrying out the determination reaction.

Figure 1:
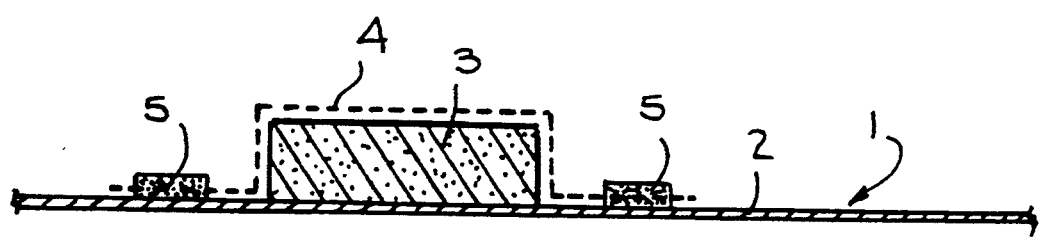
FIG. 1 is a side view of test carrier.
Figure 2:
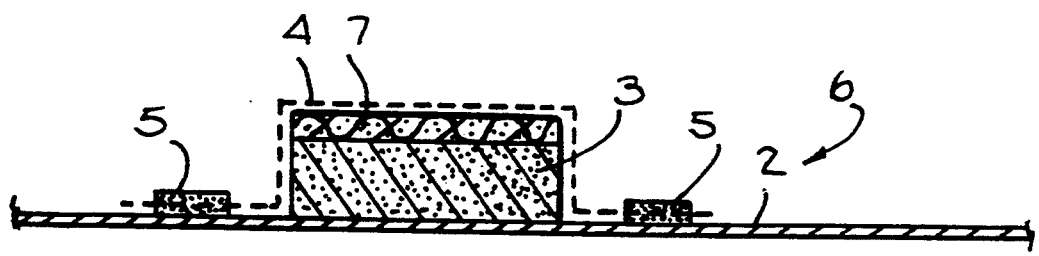
FIG. 2 is a side view of test carrier.

If, to the covering mesh (4) of the test carrier according to FIGS. 1 or 2, there is applied a hydrolase-containing solution or if the test carrier is dipped into such a solution, the sample rapidly penetrates through the covering mesh (4) and, with dissolving of the impregnated reagents, into the absorbent reagent carrier (3). In the case of the presence of hydrolases, the initially described reaction sequence takes place at the end of which a colored material is formed which can be visually assessed on the test carrier or can be measured remission photometrically and thus give a conclusion regarding the concentration of the enzyme to be determined in the sample investigated.

We have found that in the case of the use according to the present invention of the 1-arylsemicarbazides of general formula (I), a remarkable stabilization of hydrolase substrates of the initially described kind takes place. This stabilization can, in particular, be ascertained by the substantially reduced or completely absent coloration of such hydrolase substrates when they are stored alone or together with oxidation agents, for example iodates, especially in the case of an elevated temperature and under the action of light. For the achievement of a stabilization, the hydrolase substrate and the 1-arylsemicarbazide are preferably so mixed that, after contacting with the liquid to be investigated, the concentration of the 1-arylsemicarbazide of general formula (I) in the sample liquid is 0.25 to 50 mMole/liter and especially 0.5 to 20 mMole/liter, whereas the concentration of the enzyme substrate under the same conditions is 2.5 to 50 mMole/liter and especially preferably 5 to 30 mMole/liter. When the reagents are used on test carriers, for example those according to FIGS. 1 and 2 of the accompanying drawings, the above-mentioned concentrations also correspond to the concentrations of the solutions used for the impregnation of the carrier materials used.

The stabilizing effect of the 1-arylsemicarbazides of general formula (I) on hydrolase substrates of the initially described kind manifests itself not only in the neutral and alkaline medium but, in particular, also in the acid pH range from about 3.5.

Especially in the case of test carriers according to FIG. 2 of the accompanying drawings, we have found that the concentration of arylsemicarbazide can be reduced, without reducing the stabilization of the hydrolase substrate, when the reagent paper (3) contains, besides the hydrolase substrate and the 1-arylsemicarbazide, ascorbic acid or thiosulphate. However, care is thereby to be taken that the amount of oxidation agent in mesh (7) is so great that, in the case of application of the sample and subsequent mixing of the reagent components, the ascorbic acid or the thiosulphate is oxidized very quickly and then sufficient oxidation agent for the oxidation of the enzymatically-formed leuko color material is still available. By means of such an addition of ascorbic acid or thiosulphate, not only can the concentration of 1-arylsemicarbazide be reduced but also, surprisingly, there is observed a more rapid color development in the case of the hydrolase determination.

The use of 1-arylsemicarbazides of general formula (I) for stabilization has proved to be effective in particular for those hydrolase substrates which, by hydrolysis, give rise to 3-hydroxyindole or a 3-hydroxyindole substituted in the indole nucleus, for example 5-bromo-4-chloro-3-hydroxyindole.

The use of 1-arylsemicarbazides of general formula (I) has proved to be especially useful for the stabilization of hydrolase substrates of the general formula:

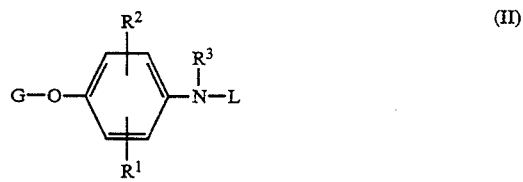

(II)

wherein G is the residue of an inorganic or organic acid or a glycoside radical, $R^1$ and $R^2$, which can be the same or different, are hydrogen or halogen atoms, $SO_3H$, $PO_3H_2$ or a salt of these acid groups, hydroxyl, nitro, carboxyl, carboxamide or cyano or alkyl, alkenyl, alkoxy, alkylsulphinyl, alkylsulphonyl, alkoxycarbonyl, alkylcarbonyl, aryl or aralkyl radicals optionally substituted one or more times by hydroxyl, carboxyl, halogen, cyano, $SO_3H$ or $PO_3H_2$ or by salt of one of these acid residues or, when the two substituents are present on neighbouring carbon atoms, together represent a 1,4-butadiendiyl radical which is optionally substituted one or more times by $SO_3H$, $PO_3H_2$ or a salt of these acid groups, an alkyl and/or a carboxyl group, $R^3$ is a hydrogen atom, —CO—COOH, $SO_3H$, $PO_3H_2$ or a salt of these acid groups, an alkylcarbonyl radical optionally substituted one or more times by halogen, COOH, $SO_3H$ and/or $PO_3H_2$ or a salt of these acid groups or an arylcarbonyl radical optionally substituted one or more times by $SO_3H$, $PO_3H_2$ or a salt of these acid groups and L is a radical of the general formula:

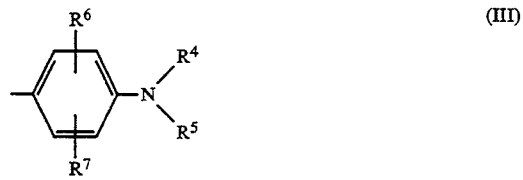

(III)

wherein $R^4$ amd $R^5$ can be the same or different and are alkyl radicals or together represent a saturated hydrocarbon chain containing 3 to 6 members which can be interrupted by oxygen, sulphur or nitrogen, whereby alkyl or the hydrocarbon chain can optionally be substituted one or more times by hydroxyl, carboxyl, alkoxycarbonyl, alkoxy, $SO_3H$ or $PO_3H_2$, a salt of these acid groups or halogen and $R^6$ and $R^7$, which can be the same or different, are hydrogen or halogen atoms, hydroxyl or carboxamido groups or alkyl, alkoxy, alkylcarbonyl, alkoxycarbonyl, aryl or aralkyl radicals optionally substituted one or more times by hydroxyl, carboxyl, halogen, $SO_3H$ or $PO_3H_2$ or a salt of these acid groups or L is a pyrazolo-heterocyclic radical of the general formula:

(IV)

wherein —X—Y—signifies —NR$^8$—CO—or —N=C-R$^9$—, in which R$^8$ is a hydrogen atom or an alkyl radical and R$^9$ is an alkyl, alkenyl, alkoxy, alkyltio, aryl, aralkyl, optionally substituted in each case by hydroxyl, dialkylphosphinyl, carboxyl, SO$_3$H, PO$_3$H$_2$, a salt ot these acid groups and/or alkoxycarbonyl; amino which is optionally substituted by one or two alkyl radicals which in turn are optionally substituted by one or more hydroxyl, carboxyl and/or alkoxycarbonyl radicals, whereby, when amino is substituted by two alkyl radicals, these radicals cen be joined together to form a ring which, apart from the nitrogen atom of the amino group, can optionally also be interrupted by oxygen, sulphur or a further nitrogen atom or amino which is optionally substituted by one or two acyl radicals, alkoxy and/or aralkoxycarbonyl radicals, H$_2$N—CO—, alkyl-, aralkyl- and/or arylcarbamoyl radicals; or is hydrogen, carboxyl, alkoxycarbonyl, carboxamido or halogen and Z signifies —NR$^{10}$—N=N—, whereby R$^{10}$ is a hydrogen atom or an alkyl or aralkyl radical, or Z is an unsaturated chain containing 3 to 5 members selected from nitrogen atoms or from carbon atoms and optionally one or more sulphur or nitrogen atoms, whereby carbon atoms are optionally substituted by alkyl, alkoxy, hydroxyalkyl, alkylthio, hydroxyl, aralkyl, aryl, carboxyl, carboxamido, alkoxycarbonyl, cyano, amino, which is optionally substituted by one or two alkyl radical optionally substituted in turn by one or more hydroxyl, carboxyl and/or alkoxycarbonyl radicals, and/or halogen, as well as nitrogen atoms which are not connected via a double bond, optionally substituted by alkyl or aralkyl or two neighbouring chain substituents optionally form an alkylene radical which, in turn, is optionally substituted or annelated with aryl or a corresponding tautomeric radical.

By an inorganic acid residue in the definition of G, in particular there is to be understood an ortho- or pyrophosphoric acid residue or a sulphuric acid residue which is connected to the aminophenol basic structure by an ester bond. Preferred are the residues PO$_3$MM′ and SO$_3$M and especially PO$_3$MM′, whereby, in the case of the free acids, M and M′ are hydrogen atoms, whereas, when the acids are present in the form of salts, M and M′ are alkali metal, alkaline earth metal or ammonium ions.

By alkali metal ions in the definition of M and M′, in particular there are to be understood lithium, sodium and potassium ions. Alkaline earth metal ions are, in particular, magnesium, calcium and barium ions.

Ammonium ions in the definition of M and M′ can be the unsubstituted ammonium ion NH$_4$+ or an ammonium ion substituted one or more times by alkyl or aralkyl radicals. In this case, an alkyl radical is to be understood to be one containing up to 6 carbon atoms, the methyl and ethyl radicals being preferred. By an aralkyl radical is to be understood one in which an alkyl radical as defined above is substituted by an aryl radical, whereby aryl is a carbon aromatic or a heteroaromatic radical and preferably one containing 6 to 10 ring atoms, especially a phenyl or naphthyl radical. The preferred aralkyl radical is the benzyl radical. The substituents of substituted ammonium ions can be the same or different. Cations of quaternised nitrogen-heterocyclic compounds can also be used as ammonium ions. Examples therefor include the piperidinium cation and the pyridinium ion.

By an organic acid residue in the definition of G are to be understood, in particular, residues of alkanecarboxylic acids, amino acids and oligopeptides which are present with the carboxyl end thereof bound as esters on the aminophenol basic structure of general formula (II).

Alkanecarboxylic acid residues in the definition of G are compounds containing up to 20 carbon atoms. Especially preferred are acetic acid, propionic acid, butyric acid, palmitic acid and stearic acid. Besides saturated acid residues, G can also be an unsaturated acid residue, for example an oleic acid, linoleic acid or linolenic acid residue.

The amino acid residue is preferably the residue of a natural α-amino acid in the L- or D-form or also in racemic form. Especially preferred are the residues of glycine, alanine, valine, leucine, isoleucine, phenylalanine and thyrosine, whereby, in each case, the L-form is quite especially preferred.

By an oligopeptide residue is to be understood, for example, a di-, tri-, tetra- or pentapeptide and preferably a di- or tripeptide, whereby, as amino acid component, the above-mentioned amino acids are preferably used.

The amino groups of the amino acid or oligopeptide residues attached in the manner of esters to the aminophenol radical can be present in free or protected form. As protective groups are here to be understood all the conventional amino protective groups, especially acyl, oxycarbonyl, thiocarbonyl, sulpho, sulphino, vinyl, cyclohexenyl, phosphoryl or carbamoyl group. Especially preferred amino protective groups are the tosyl, benzyloxycarbonyl and tert.-butoxycarbonyl radicals.

A glycoside radical in the definition of G can be a mono- or oligosaccharide. The sugar residue can be attached to the aminophenol basic structure either α- or β-glycosidically. Examples of preferred monosaccharides are galactose, glucose and mannose. N-acetylglucosamine is especially preferred and quite especially preferred is β-glycosidically-bound N-acetyl-2-D-glucosamine.

However, oligosaccharides can also be used as sugar residues. Those compounds are designated as oligosaccharides which are made up of 2 to 10 and preferably 2 to 7 monosaccharide units, the heptaoses being especially preferred.

Of the group of the organic and inorganic acid residues and of the glycoside residues in the meaning of G, the glycoside residues are preferred for compounds of general formula (II). The N-acetylglucosamine residue is quite especially preferred because such N-acetyl-β-D-glucosaminidase substrates are especially well stabilized by the 1-arylsemicarbazides of general formula (I).

Insofar as nothing is stated to the contrary, the following radicals having the following meanings in the general formulae used herein : "alkyl" alone and also in alkylsulphinyl, alkylsulphonyl, alkylcarbonyl, alkylthio, alkylcarbamoyl, alkylamino, dialkylphosphinyl and aralkyl radicals means a straight-chained or branched alkyl radical containing up to 6 and preferably up to 4 carbon atoms. Examples thereof include the methyl, ethyl, propyl, isobutyl and tert.-butyl radicals.

When an amino group is substituted by two alkyl radicals, these radicals can also be joined to form a ring in such a manner that, in all, they represent a ring interrupted by a nitrogen atom. Those amino groups are thereby preferred which represent a ring containing in all 5 or 6 members and which, in turn, can be interrupted by oxygen, sulphur or another nitrogen atom. The morpholino radical is especially preferred. A hydroxyalkyl radical is an alkyl radical containing up to 6 and preferably up to 4 carbon atoms which is substituted by a hydroxyl group. The hydroxyalkyl radical can be the residue of a primary, secondary or tertiary alcohol. The 2- and 1-hydroxyethyl and the hydroxymethyl radicals are especially preferred.

"Alkoxy" alone and also in alkoxycarbonyl and aralkoxycarbonyl radicals are alkoxy radicals containing up to 6 and preferably up to 4 carbon atoms. Examples thereof include the methoxy, ethoxy, propoxy, isobutoxy and tert.-butoxy radicals.

"Aryl" alone and also in arylcarbonyl and arylcarbamoyl radicals means a carbon aromatic or a heteroaromatic radical, preferably containing 6 to 10 ring atoms and especially a phenyl or napthyl radical which can additionally be substituted by alkyl, alkoxy and/or halogen, the phenyl radical being especially preferred.

An "aralkyl" radical alone or also in an aralkylcarbamoyl radical means a radical in which an alkyl radical as defined hereinbefore is substituted by an aryl radical, the benzyl radical being preferred.

An "aralkoxy" radical, for example in an aralkoxycarbonyl radical, means a radical in which an alkoxy radical as defined hereinbefore is substituted by an aryl radical, the benzyloxy radical being preferred.

"Halogen" stands for fluorine, chlorine, bromine or iodine, fluorine and chlorine being preferred.

"Alkenyl" means an unsaturated hydrocarbon radical containing 2 to 6 and preferably 2 to 4 carbon atoms, the vinyl and allyl radicals being preferred.

An acyl radical is a carboxylic acid residue which can contain alkyl, aralkyl or aryl moieties, the acetyl, phenylacetyl and benzoyl radicals being preferred.

By an alkylene radical is to be understood a straight-chained or branched, saturated or unsaturated hydrocarbon chain containing 3 to 5 and preferably 3 or 4 carbon atoms with two free bond positions. Examples therefor include —CH$_2$—CH=CH—,

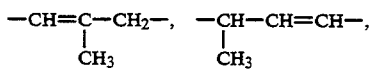

—(CH$_2$)$_4$— and —CH=CH—CH=CH. The butadiendiyl radical (—CH=CH—CH=CH—) and the tetramethylene radical (—(CH$_2$)$_4$—) are preferred. By a dialkylphosphinyl group is to be understood the radical

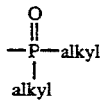

wherein alkyl has the meaning as herein before described, the dimethylphosphinyl radical being preferred.

As salts of SO$_3$H, PO$_3$H$_2$ and carboxyl groups, there can be used alkali metal and alkaline earth metal salts, as well as ammonium salts. By alkali metal salts are to be understood lithium, sodium, potassium, rubidium and caesium salts, preferably lithium, sodium and potassium salts and especially sodium and potassium salts. Alkaline earth metal salts are those of beryllium, magnesium, calcium, strontium and barium, preferably of magnesium and calcium, the calcium salts being especially preferred. As ammonium salts, there can be used those of the unsubstituted ammonium ion NH$_4^+$. However, it is also possible to use those ammonium salts in which the ammonium ion is substituted up to 4 times by alkyl, aryl or aralkyl radicals. For these radicals, there apply the definitions given hereinbefore, whereby, as alkyl radicals, methyl, ethyl and n-propyl are preferred, as aryl radical the phenyl radical is preferred and as aralkyl radical the benzyl radical is preferred. As ammonium ions there can also be used cations of quaternised nitrogen heterocyclic compounds, examples thereof including the piperidinium cation and the pyridinium ion.

As carboxamido radical there is to be understood the —CONH$_2$ radical but also those radicals in which the amino group is substituted by one or two alkyl radicals which are optionally substituted in turn by one or more hydroxyl, carboxyl and/or alkoxycarbonyl radicals.

Especially advantageous are those hydrolase substrates in which R$^3$ is a hydrogen atom or an alkylcarbonyl radical substituted one or more times by halogen and preferably the trifluoroacetyl radical. Hydrogen is quite especially preferred for the meaning of R$^3$.

Compounds of the general formula (II) in which L is a pyrazolo-heterocyclic radical of general formula (IV) are especially well stabilized according to the present invention. Of these, those are especially preferred in which Z is so positioned that at least one double bond of the unsaturated chain is in conjugation with the double bond or with the nitrogen atom in general formula (IV).

Furthermore, compounds of general formula (II) especially preferred in which L is a pyrazolo-heterocyclic radical of general formula (IV), whereby in the unsaturated chain Z, if this contains nitrogen atoms which are not connected via a double bond, these are substituted by alkyl or aralkyl radicals.

For radicals of general formula (IV), tautomeric forms are also possible. These are also to be considered to be included by general formula (IV).

Compounds of the general formula (II) which are preferably stabilizable according to the present invention are those in which the radical I is one selected from the following groups of general formulae (V) to (XVI):

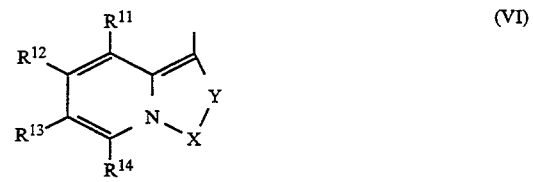

(VI)

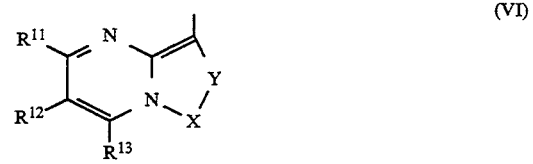

(VI)

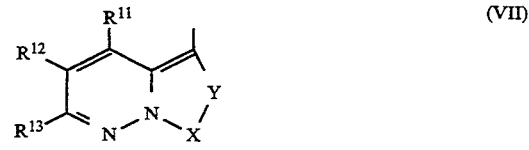

(VII)

-continued

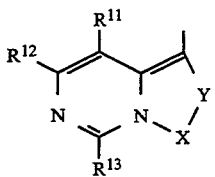 (VIII)

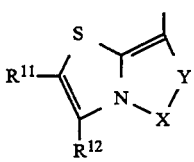 (IX)

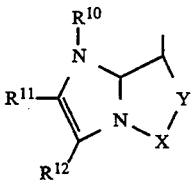 (X)

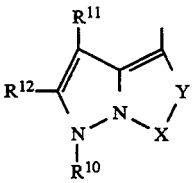 (XI)

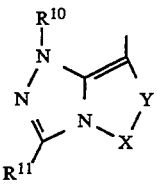 (XII)

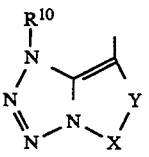 (XIII)

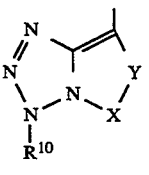 (XIV)

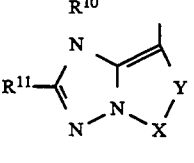 (XV)

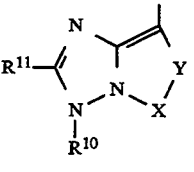 (XVI)

as well as posibly the corresponding tautomeric forms.

X-Y and $R^{10}$ hereby have the same meanings as given hereinbefore. $R^{11}$, $R^{12}$, $R^{13}$ and $R^{14}$, which can be the same or different, stand for hydrogen, hydroxyl, alkyl, alkoxy, alkylthio, aralkyl, aryl, carboxyl, alkoxycarbonyl, carboxamido, cyano, amino, which is optionally substituted by one or two alkyl radicals which, in turn, can be substituted by one or more hydroxyl, carboxyl and/or alkoxycarbonyl radicals, or halogen, whereby two neighbouring radicals can optionally form an alkylene radical which, in turn, is optionally substituted or anellated with aryl. The definitions of the radicals correspond to those given hereinbefore.

Substances which are especially preferably stabilisable according to the present invention are those of general formula (II) in which L stands for a radical from those of general formulae (V), (VI), (VII), (IX), (X) and (XII) and possibly of the corresponding tautomeric forms. Quite especially preferred are those compounds in which X-Y has the meaning N=CR$^9$, whereby R$^9$ can have the meaning given for general formula (IV) but is preferably a hydrogen atom or an alkoxy radical.

Outstandingly stabilized in the meaning of the present invention are especially the β-glycosidically-bound N-acetyl-D-glucosaminides of (4-hydroxyphenyl)-(2-methylpyrazolo[1,5-a]pyridin-3-yl)-amine and (4-hydroxyphenyl)-(pyrazolo[1,5-a]pyridin-3-yl)-amine.

The compounds of general formula (II) can be prepared by reacting a leuko azomethine coloured material of the general formula:

$$\text{(XVII)}$$

wherein $R^1$–$R^3$ and L have the same meanings as given for general formula (II) and A is a hydrogen atom, an optionally substituted ammonium ion or an alkali metal, with a compound of the general formula:

$$G\text{—}D \qquad \text{(XVIII)}$$

in which G is an organic or inorganic acid residue or a glycoside radical in the meaning given for general formula (II), whereby functional groups present in the glycoside radical, for example amino and/or hydroxyl groups, are optionally substituted with protective groups conventional in peptide and carbohydrate chemistry, and D is a reactive group, and protective groups are possibly subsequently split off.

By an unsubstituted ammonium ion is to be understood NH$_4^+$. This ion can optionally be substituted in the meaning of A in general formula (XVII) also by alkyl or aralkyl radicals, as have been characterised hereinbefore, one or more times. The substituents of substituted ammonium ions can be the same or different. As ammonium ions there can also be used cations of quaternised nitrogen heterocyclic compounds, examples herefor including the piperdinium cation and the pyridinium ion.

The alkali metal in the meaning of A in general formula (XVII) is especially lithium, sodium or potassium, sodium thereby being particularly preferred.

D means a reactive group which is able to react with the phenol or phenolate group OA of the general formula (XVII). The choice of the reactive group depends upon the nature of the radical G. If G is a sugar residue, then D is preferably a readily substitutable radical, for example an acetyl radical or a halogen atom, which can be selected from the group fluorine, chlorine, bromine and iodine, in which case chlorine, bromine and iodine are preferred.

As protective groups which are conventional in carbohydrate chemistry, there are to be especially mentioned the acetyl, benzoyl, benzyl and trimethylsilyl radicals.

When G means an amino acid or peptide residue which is to be esterified with its carboxyl end with an aminophenol of general formula (XVII), then, as reactive group D, there can be used a group which is conventional in peptide chemistry. As reactive derivatives, there are used, for example, acid halides, preferably acid chlorides, or the mixed anhydrides and active esters usually employed in peptide syntheses. The same reactive groups can also be used for the binding of alkanecarboxylic acids to the aminophenol structure.

When G is an inorganic acid residue, compounds of the general formula (XVII) are preferably reacted with the corresponding acid halides and especially acid chlorides.

In every case, in the case of an esterification, care is to be taken, when $R^3$ in general formula (XVII) is a hydrogen atom, to substitute this amino group, before carrying out the esterification reaction, with a protective group, for example one conventionally used for this purpose in peptide chemistry, and subsequently again to remove this protective group.

By way of example, the process for the preparation of compounds of general formula (II) is illustrated using the example of the especially preferably stabilizable compounds in which G is an N-acetyl-$\beta$-D-glucosaminide radical. This process can also be used correspondingly for the preparation of other glycoside derivatives of general formula (II).

N-Acetyl-$\beta$-D-glucosaminidyl derivatives of general formula (II) can be prepared in that, as compound of general formula (XVIII), a compound of the general formula:

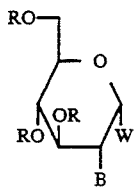

(XIX)

wherein W is a halogen atom, R is a hydroxyl protective group conventional in carbohydrate chemistry, B is an azide group, a protected amino group or an —NH—COCH$_3$ radical or B and W together represent the group

is reacted with a compound of the general formula:

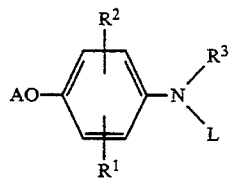

(XVII)

wherein $R^1$–R3 and L have the same meanings as given for general formula (II) and A is a hydrogen atom, an optionally substituted ammonium ion or an alkali metal, when B is a protected amino group the amino protective group is removed or when B is an azide group this is converted by reduction into an amino group and the amino group is converted by acetylation into the —NHCOCH$_3$ radical and subsequently the hydroxyl protective groups are split off.

One possibility is, for example, to react a leuko azomethine colored material of general formula (XVII) with the previously given meaning with a per-O-substituted 1-halo-N-acetylglucosamine of the general formula:

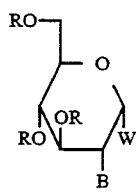

(XIX)

wherein W is a halogen atom, B is an —NHCOCH$_3$ radical and R is a protective group conventional in carbohydrate chemistry, with Walden inversion on the C-1 atom of the sugar residue, to give a per-O-substituted $\beta$-glycoside and to split off the hydroxyl protective groups from the latter by known methods.

The reaction of the compounds of general formulae (XVII) and (XIX) with the previously mentioned meaning to give N-acetyl-$\beta$-D-glucosaminides of general formula (II) is preferably carried out in the presence of acid receptors, for example alkali metal hydroxides, carbonates or bicarbonates, in aqueous acetone or under phase transfer conditions in a water/benzene or water/chloroform mixture (cf. Synthesis, 223/1988).

Furthermore, the N-acetyl-$\beta$-D-glucosaminides of general formula (II) can be prepared by converting the leuko azomethine colored materials of general formula (XVII), wherein A is a hydrogen atom, first with an alkali metal hydroxide or alcoholate into the alkali metal salt or with an optionally substituted amine into an ammonium salt, whereby the alkali metal and the ammonium ion can have the meaning given hereinbefore, and then reacting this in a dipolar aprotic solvent, for example acetone, dimethyl sulphoxide, dichloromethane or dimethylformamide, with the per-O-substituted 1-halo-N-acetylglucosamines.

Furthermore, in the case of the synthesis of N-acetylglucosaminides of general formula (II) from leuko azomethine colored materials of general formula (XVII) and 1-halo-N-acetylglucosamines, additions of individual silver salts or mixtures of silver salts (silver oxide, carbonate on Celite ®, triflate, salicylate) and/or of individual mercury salts or mixtures of mercury salts (mercury bromide, cyanide, acetate, oxide), optionally with the use of drying agents, for example calcium chloride or Drierit®, in solvents, for example methylene chloride, chloroform, benzene, toluene or dioxan, have proved to be useful.

In addition, an oxazoline of general formula (XIX), in which B and W together form the group

can be used in the presence of an organic acid, for example p-toluenesulphonic acid or a Lewis acid, such as boron trifluoride ethereate, or ferric chloride, for the synthesesw of N-acetylglucosaminides of general formula (II). Examples of such glycosidation reactions are described in Carbohydrate Research, 136, 309–323/1985 and 64, 334–338/1978.

Finally, processes for the preparation of the N-acetyl-glucosaminides of general formula (II) can be carried out in which, in the compound of general formula (XIX), B is an amino group substituted with a protective group, for example a benzyloxycarbonyl, allyloxycarbonyl, dichloroacetamido or phthalimido radical, or an appropriate substituent stable under the glycosidation conditions from which an amino group can be liberated, for example an azide group. The glycosidation reaction is carried out, by splitting off the protective groups according to the methods of peptide chemistry or reduction of an azido group the amino group is liberated which, in a final step, is selectively N-acetylated (cf. for example J. Org. Chem., 32, 3767/1967).

The splitting off of the protective groups takes place in the manner known from carbohydrate chemistry by hydrogenolysis in the case of protective groups of the benzyl type, by the action of sodium methylate, sodium cyanide or sodium bicarbonate in methanol for splitting off acyl radicals, for example acetyl radicals. The methods of splitting off protective groups are described in Adv. Carbohydr. Chem. Biochem., 39, 13/1981.

The synthesis of 1-halo-N-acetylglucosamines is described, for example, in Org. Synth., 46, 1; Methods in Carbohydrate Chem., 6, 282/1972 and J. Crg. Chem., 26, 445/1961.

The leuko azomethine colored materials required for the preparation of the compounds of general formula (II) and having the general formula:

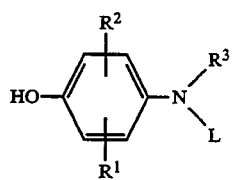
(XVII')

in which R¹–R³ and L have the meanings given for general formula (II), whereby L is preferably a pyrazolo-heterocyclic radical of the general formula:

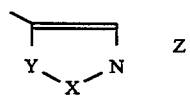
(IV)

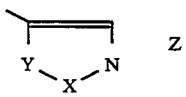
(IV)

in which X-Y and Z have the meanings already given for the corresponding compounds of general formula (II), can be prepared by reduction of the corresponding colored materials of the general formula:

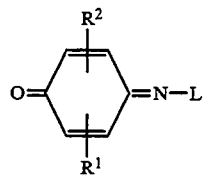
(XX)

wherein R¹, R² and L have the meanings given for the compounds of general formula (XVII'), according to known methods with reducing agents, for example catalytic hydrogenation, sodium borohydride, palladium/-hydrazine or sodium dithionite. Such reducing agents are described in Houben-Weyl, Vol. 4/1c and 4/1d.

Acyl groups R³, such as are stated for compounds of general formula (II), can be introduced either at the stage of the leuko colored material of general formula (XVII') where R³ means hydrogen or of the protected per-O-substituted N-acetyl-glucosaminide, such as occurs in the case of the preparation of compounds of general formula (II) in which G is glycoside. There are used activated acid derivatives, for example halides, anhydrides, mixed anhydrides, such as are known from peptide chemistry.

The colored materials of general formula (XX) required for the preparation of compounds of general formula (XVII') can be most preferably prepared by the oxidative coupling of an amino compound of the general formula:

NH₂—L     (XXI)

wherein L has the meaning given for general formula (II) but is preferably a pyrazolo-heterocyclic radical of general formula (IV), in which X-Y and Z have the meanings given for the compounds of general formula (II), with a phenol of the general formula:

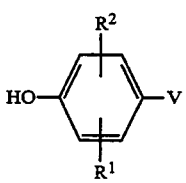
(XXII)

wherein R¹ and R² have the meanings given for the compounds of general formula (II) and V is a hydrogen or halogen atom, carboxyl or SO₃H. For this purpose, an amino compound of general formula (XXI) and a phenol of general formula (XXII), preferably with V being a hydrogen atom, are reacted in the presence of an oxidation agent, for example potassium ferricyanide, potassium persulphate, potassium hydrogen persulphate, iodine, hydrogen peroxide/peroxidase, lead dioxide, NaOCl, NaOBr, or an organic oxidation agent, for example N-bromosuccinimide or related compounds.

Furthermore, the colored materials of general formula (XX) can also be prepared by reacting N-haloimines of the general formula:

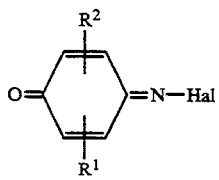 (XXIII)

wherein $R^1$ and $R^2$ have the meanings given for the compounds of general formula (II) and Hal is a halogen atom, whereby the halogen atom is fluorine, chlorine, bromine or iodine and preferably chlorine, with compounds of the general formula:

 (XXIV)

wherein L has the meaning given for general formula (II) but is preferably a pyrazolo-heterocyclic radical of general formula (IV), whereby X-Y and Z have the meanings given for compounds of general formula (II).

The reaction conditions can be chosen analogously to those described in Houben-Weyl, Vol. 7/b, pp 296 et seq.

For the amino compounds of general formula (XXI), there are the following methods of preparation. When L is a radical of general formula (III), as is defined for compounds of general formula (II), these amino compounds are known or can be prepared analogously to the known compounds. Usually, N,N-disubstituted anilines are used as starting materials which are nitrosated. Reduction of the nitroso group gives p-phenylenediamine derivatives of general formula L-NH$_2$ (see J.A.C.S., 73, 3100/1951).

Compounds of general formula (XXI), wherein L is a pyrazolo-heterocyclic radical of general formula (IV), can be prepared analogously to known methods in that a compound of general formula (XXIV), in which L is a pyrazolo-heterocyclic radical of general formula (IV), is converted according to known methods into the corresponding amino compound. This can be
a) by reaction with nitric acid or nitric acid in admixture with sulphuric acid and/or acetic anhydride to give the corresponding nitro compound or
b) by reaction with nitrous acid to give the corresponding nitroso compound or
c) by reaction with an aromatic diazonium salt to give the corresponding arylazo compound
and subsequent reduction. Nitro, nitroso and arylazo (i.e. aryl-N=N.) radicals, wherein aryl can have the same meaning as already explained for aryl radicals and other groups containing such radicals, can be converted by reduction with reagents such as zinc in acid, for example hydrochloric acid or glacial acetic acid, sodium dithionite, tin in acid, for example hydrochloric acid, stannous chloride or by catalytic hydrogenation, for example over palladium/carbon to give the amino compounds. Such reactions are described in Houben-Weyl, Methoden der organischen Chemie, Vol. 11/1, pp. 341 et seq.

The introduction of nitro, nitroso or arylazo groups starting from compounds of general formula (XXIV) can take place by nitration with nitric acid or nitric acid in admixture with concentrated sulphuric acid or acetic anhydride.

By nitrosation with nitrous acid or by azo coupling with aromatic diazonium salts, the nitroso group or an arylazo group can be introduced. Examples for such reactions are described in Houben-Weyl, Methoden der organischen Chemie, Vol. 10/1 and 10/3.

If heterocyclic compounds of general formula (XXIV) are present in which H is not a hydrogen atom but rather a carboxyl, alkoxycarbonyl or alkylcarbonyl radical, then these can be converted by hydrolysis with concentrated hydrochloric acid and, in the case of carboxylic acids, by thermal decarboxylation into compounds of general formula (XXII). This is then followed by the introduction of a nitro, nitroso or arylazo group.

Nitrogen atoms which are not attached to a double bond and which are present in radicals X-Y or Z of general formula (IV) can optionally be alkylated ar aralkylated. The N-alkylation of N-aralkylation can be carried out by reaction of the corresponding compounds of general formula (XXIV) but preferably those heterocyclic compounds in which H is not a hydrogen atom but rather a nitro, nitroso, alkoxycarbonyl, acyl or arylazo group, with alkylation or aralkylation agents, for example alkyl or aralkyl halides, dialkyl or diaralkyl sulphates or arylsulphonic acid alkyl esters or aralkyl esters in the presence of a base, such as sodium hydride, tertiary amines, alkali metal carbonates or sodium hydroxide, in a solvent, such as dimethylformamide or aqueous-alcoholic systems.

The required starting compounds of general formula (XXIV) or those compounds corresponding to general formula (XXIV), in which H is replaced by alkoxycarbonyl or acyl, whereby L is a pyrazolo-heterocyclic radical of general formula (IV), have either already been described or can be synthesized analogously to these known compounds. Information regarding the preparation of heterocyclic systems are given in the following publications: G. I. Ellis, "Synthesis of fused Keterocycles" in "The Cehmistry of Heterocyclic Compounds", E. C. Taylor ed., 1987, pub. John Wiley and sons; P. N. Preston, "Condensed Imidazoles" in "The Chemistry of Heterocyclic Compounds", A. Weissberger and E. C. Taylor eds., 1986, pub. John Wiley and Sons; Adv. of Het. Chem., 36, 343/1984; Chem. Pharm. Bull., 22, 482/1974; J. Het. Chem., 12, 481/1975; Chem. Pharm. Bull., 22, 1814/1974; Ann. 660, 104/1962. Chem. Pharm. Bull. 23. 452/1975; J. Het. Chem. 10, 411/1973; J. Chem. Soc., Perkin I, 2047/1977

The following Examples are given for the purpose of illustrating the present invention:

EXAMPLE 1

1.1  (4-Hydroxyphenyl)-(2-methylpyrazolo[1,5-a]Pyridin-3-yl)-amine

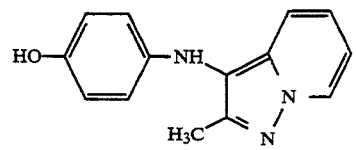

1.1.1 7 g. 3-acetyl-2-methylpyrazolo [1,5-a]pyridine (see J. Crg. Chem., 42, 443/1977) are dissolved in 140 ml. 6N hydrochloride acid and mixed dropwise at 0° C. with a solution of 5.52 g. sodium nitrite in water. After 2 hours, the ice-bath used is removed, the reactive mixture is left to stand overnight at ambient temperature and then adjusted to pH 9. The precipitated nitroso compound (6.4 g.) is filtered off with suction and dissolved in about 150 ml. 2N hydrocloric acid. The solution of the nitroso compound is mixed with 15 g. stannous chloride dihydrate and stirred for 1 hour at ambient temperature. For the completion of the reaction, 6 g. stannous chloride dihydrate in 20 ml. concentrated hydrochloric acid are then again added thereto. The crude product is chromatographed on silica gel with ethyl acetate. The product-containing fractions are evaporated, the residue is dissolved in ethanol and mixed with ethanolic hydrochloric acid. The precipitate which separates out after some time is filtered off with suction and dried. There are obtained 3.1 g. (45% of theory) 3-amino-2-methylpyrazolo[1,5-a]-pyridine hydrochloride; m.p.>275° C.; R$_f$ (silica gel; ethyl acetate/acetone/glacial acetic acid/water, 50:25:12.5:12.5 v/v/v/v)=0.6.

1.1.2 2.82 g. phenol are dissolved in 75 ml. pyridine and the solution is mixed with 450 ml. water. A solution of 5.5 g. 3-amino-2-methylpryazolo[1,5-a]pyridine hydrochloride from 1.1.1 in 150 ml. water is then added thereto and the reaction mixture is subsequently mixed, while stirring, with a solution of 78 g. potassium ferricyanide in 450 ml. water. The precipitated blue-colored material is filtered off with suction, washed with water and dried. Yield 4.85 g.

TLC (silica gel, ethyl acetate/methylene chloride 1:1 v/v): R$_f$=0.5.

1.1.3 For reduction to the leuko colored material, the colored material is dissolved in 200 ml. ethyl acetate and the solution is mixed with about 100 ml. saturated aqueous sodium carbonate solution. The solution is mixed, while vigorously shaking, with sodium dithionite until it is decolorized. The organic phase is separated off, dried and evaporated to a small volume. It is mixed with ligroin and the precipitate obtained is filtered off with suction, washed with ligroin and subsequently dried. There are obtained 4.45 g. of the title compound which is pure enough for further working up. A purification by chromatography over silica gel with methylene chloride/methanol (98:2 v/v) is possible.

R$_f$ (silica gel, ethyl acetate/methylene chloride 1:1 v/v)=0.6

R$_f$ (silica gel, methylene chloride/methanol 95:5 v/v)=0.3.

1.2 N-Acetyl-β-D-glucose-2-aminide of (4-hydroxyphenyl)-(2-methylpyrazolo[1,5-a]pyridin-3-yl)-amine

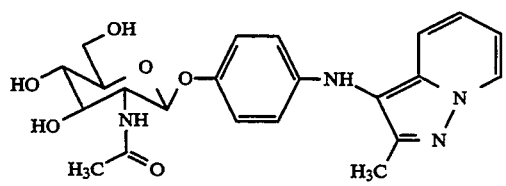

1.2.1 2.6 g. of the leuko colored material obtained in 1.1, 8.83 g. 2-acetamido-3,4,6-tri-O-acetyl-2-deoxy-α-D-glucosyl chloride and 4.21 g. benzyltriethylammonium bromide are introduced into a mixture of 125 ml. chloroform and 125 ml. water. The mixture is vigorously stirred, mixed with 8.7 g. potassium carbonate and boiled under reflux for 6 hours, whereby after 3 hours 4.4 g. of the halogenose and 4.3 g. potassium carbonate are again added. The chloroform phase is separated off, dried with anhydrous sodium sulphate and evaporated. The residue is chromatographed on silica gel with ethyl acetate. The product-containing fractions are evaporated.

1.2.2 460 mg. of the protected sugar derivative obtained in 1.2.1 are dissolved in 10 ml. methanol, mixed with 0.9 g. sodium bicarbonate and vigorously stirred for 3 hours at ambient temperature. The reaction mixture is filtered, the filtrate is evaporated and the residue is chromatographed on silica gel with ethyl acetate/methanol (8:2 v/v). The product-containing fractions are combined and evaporated. The residue is taken up in a little methanol and the solution is mixed with diethyl ether. The precipitate so obtained is filtered off with suction and washed with diethyl ether. The title compound is obtained with an m.p. 188°–191° C.; R$_f$(silica gel, toluene/acetic acid/ethyl acetate/methanol 1:1:1:1 v/v/v/v)=0.35.

EXAMPLE 2

2.1 (4-Hydroxyphenyl)-(pyrazolo[1,5-a]-pyridin-3-al)-amine

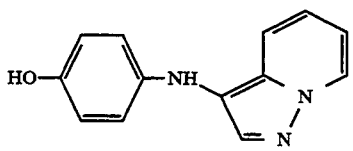

2.1.1 2 g. Pyrazolo[1,5-a]pyridine (Ann. Chem., 498/1977) are dissolved in 30 ml. 6N hydrochloric acid, the solution is cooled to 0° C. and a solution of 6.9 g. sodium nitrite in 30 ml. water is slowly added dropwise thereto. After 1 hour, the nitrosation is ended. One adds to the reaction mixture about 100 ml. water and extracts repeatedly with ethyl acetate. The organic phase is dried and evaporated. There are obtained 9.6 g. 3-nitroso-pyrazolo[1,5-a]pyridine 2.1.2 9 g. of the nitroso compound obtained according to 2.1.1 are introduced into a solution of 22 g. stannous chloride dihydrate in 180 ml. concentrated hydrochloric acid. The reaction mixture is stirred for 1 hour at ambient temperature and, for completion of the reduction, mixed with 8 g. stannous chloride dihydrate in 30 ml. concentrated hydrochloric acid. The suspension is poured on to about 150 g. ice, adjusted with sodium hydroxide to pH 12 and quickly extracted with ethyl acetate. The ethyl acetate phase is dried and evaporated. The residue is dissolved in about 350 ml. diethyl ether and mixed with ethereal hydrogen chloride. The precipitate obtained is filtered off, washed with diethyl ether and dried. There are obtained 11.3 g. (100% of theory) 3-amino-pyrazolo[1,5-a]pyridine hydrochloride with the m.p. 228°–232° C.

R$_f$(silica gel, ethyl acetate/methanol 9:1 v/v)=0.52.

2.1.3 The leuko coloured material 4-hydroxyphenyl-pyrazolo[1,5-a]pyridin-3-yl)-amine is obtained analogously to 1.1.2 and 1.1.3 with the use of 3-aminopyrazolo[1,5-a]pyridine as starting material.

R$_f$ (silica gel, ethyl acetate/diethyl ether 1:1 v/v)=0.68.

2.2 N-Acetyl-β-D-glucose-2-aminide of (4-hydroxyphenyl)-(pyrazolo[1,5-a]pyridin-3-yl)-amine

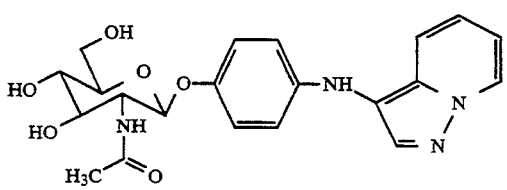

The title compound is obtained from the leuko colored material obtained in 2.1 and 2-acetamido-3,4,6-tri-O-acetyl-2-deoxy-α-D-glucosyl chloride analogously to Example 1.2; m.p. 143° C.; R$_f$(silica gel, toluene/ethyl acetate/methanol 2:1:1 v/v/v)=0.27.

EXAMPLE 3 a) A filter paper of the firm Schleicher and Schüll (23 SL) is successively impregnated with the following solutions and dried

| 1. citrate buffer | 200 mMole/liter, pH 5.0 |
|---|---|
| potassium iodate | 20 mMole/liter |
| 2. phenylsemicarbazide | 3 mMole/liter |
| hydrolase substrate from Example 1 in methanol | 10 mMole/liter | b) Impregnation as in Example 3a) but using methyl semicarbazide (1.5 mMole/liter) as stabilizer.

When the test papers from Examples 3a) and 3b) are dipped into urine which does not contain any N-acetyl-β-D-glucosaminidase (β-NAGase) or when urine is dropped on to the test papers, then the test papers do not color over the course of 10 minutes. If the urine contains a β-NAGase concentration of about 20 U/liter, then, after about 5 minutes, a distinct coloration of the test papers is obtained.

When test strips are prepared analogously to Examples 3a) and 3b) but without stabilizer then comparable results are initially obtained but, after storage for a week at 45° C., the test strips are red colored. After this time, stabilized test strips are comparable with newly produced test strips.

EXAMPLE 4 a) A filter paper of the firm Schleicher and Schüll (23 SL) is successively impregnated with the following solutions and dried:

| 1. citrate buffer | 100 mMole/liter, pH 5.0 |
|---|---|
| potassium iodate | 20 mMole/liter |
| 2. phenylsemicarbazide | 10 mMole/liter |
| hydrolase substrate from Example 2 in methanol | 10 mMole/liter | b) Impregnation as in Example 4a) but with the use of methyl-phenylsemicarbazide as stabilizer.

When test papers from Examples 4a) and 4b) are dipped into urine which does not contain β-NAGase or when urine is dropped on to the test papers, the test papers do not color after 10 minutes. When the urine contains a β-NAGase concentration of about 20 U/liter, then, after about 5 minutes, a distinct coloration of the test papers is obtained.

When test strips are produced analogously to Examples 4a) and 4b) but without stabilizer then initially comparable results are obtained but, after storage for a week at 45° C., the test strips are red colored. Stabilized test strips are, after this time, comparable with newly produced test strips.

EXAMPLE 5

A result analogous to that of Examples 3 and 4 is also obtained when a teststrip according to FIG. 2 of the accompanying drawings is produced:

The reagent paper (3)(filter paper 23 SL of the firm Schleicher and Schüll) is impregnated
a) analogously to Example 3a)
b) analogously to Example 3b)
c) analogously to Example 4a)
d) analogously to Example 4b)
but without potassium iodate.

The mesh (7)(NY 75 HC of the Züricher Beuteltuchfsbrik Zürich, Switzerland, with a filament thickness of 60 μm.) is impregnated with an aqueous solution of potassium iodate (40 mMole/liter) and dried. Reagent paper (3) and mesh (7), each with a size of 6×6 mm., are so fixed with a covering mesh (4) of the same material as mesh (7) on to a stiff polystyrene film (100×6 mm.) by means of a melt adhesive (5) that the oxidation mesh (7) is present between the reagent paper (3) and the covering mesh (4).

When the so produced test strips are dipped into urine which does not contain β-NAGase or when urine is dropped on to the covering mesh (4), then the test strips do not color over the course of 10 minutes. When the urine contains a β-NAGase concentration of about 20 U/liter, a distinct coloration of the reagent paper is obtained after about 5 minutes.

When test strips are produced in the above-described manner but without stabilizer, then comparable results are initially obtained which, however, after storage for a week at 45° C., give red-colored test strips. After this time, stabilized test strips are comparable with newly produced test strips.

EXAMPLE 6

A test carrier according to FIG. 2 of the accompanying drawings is produced analogously to Example 5, use being made of the hydrolase substrate from Example 2. However, the pre-impregnation of the reagent paper takes place with a solution of ascorbic acid.

The reagent paper (3) is successively impregnated with the following solutions and dried:

| 1. citrate buffer | 200 mMole/liter, pH 5.0 |
|---|---|
| ascorbic acid | 3 mMole/liter |
| 2. phenylsemicarbazide | 0.5 mMole/liter |
| hydrolase substrate from Example 2 in methanol | 10 mMole/liter |

The oxidation mesh (7) is impregnated with an aqueous solution of potassium iodate (40 mMole/liter).

Here, too, in the case of using a stabilizer according to the present invention, there is ascertained a stabilization of the hydrolase substrate on the test carrier in comparison with those without a stabilizer.

By means of the addition of ascorbic acid to the reagent paper (3), the concentration of semicarbazide necessary for the stabilization can be distinctly reduced. Furthermore, a quicker test system is obtained.

A comparable result is also obtained when ascorbic acid is replaced by sodium thiosulphate.

EXAMPLE 7

A paper of the firm Schleicher and Schüll (23 SL) is impregnated in the following way:

1. Pre-impregnation with 65 g. boric acid and 21 g. sodium hydroxide in 1 liter of water, adjusted with 1N hydrochloric acid to pH 8.0.
2. Main impregnation of the pre-impregnated fleece with a solution which, in 1 liter of ethanol, contains 0.78 g. 3-(N-toluene-4-sulphonyl-L-alanyloxy)-indole(prepared according to European Patent Specification No. 0,012,957, Example 7), 21.7 ml. decanol and 10 mMole/liter phenyl semicarbazide.

When a solution of leukocytes is dropped on to this reagent paper, then the paper becomes blue colored.

When test papers are prepared analogously to the above-described procedure but without stabilizer, then initially comparable results are obtained. However, in the case of a stressing time of 3 weeks at 45° C., the paper becomes bluish whereas papers with stabilizer remain white.

EXAMPLE 8

A paper of the firm Schleicher and Schüll (23 SL) is impregnated as follows:

1. pre-impregnation with hepes buffer, 50 mMole/liter, ph 7.5
2. main impregnation with 1 mMole/liter 5-bromo-4-chloro-3-indolyl-$\beta$-D-galactopyranoside (Sigma Chemie GmbH, Deisenhofen, Germany) and 10 mMole/liter phenyl semicarbazide in methanol.

When a solution of $\beta$-D-galactosidase is dropped on to the paper, a blue coloration is obtained. If test papers are produced without the stabilizer, then the results are initially comparable. However, in the case of a stressing time of 3 weeks at 45° C., the papers become bluish colored, whereas papers with stabilizer remain white.

It will be understood that the specification and examples are illustrative but not limitative of the present invention and that other embodiments within the spirit and scope of the invention will suggest themselves to those skilled in the art.

I claim:

1. A hydrolase enzyme substrate stabilized by a 1-arylsemicarbazide stabilizer of the formula Ar—NHNHCONH$_2$ wherein Ar is an unsubstituted aryl radical or is aryl substituted by alkyl, alkoxy or halogen for a reaction wherein a leuko color substance is formed from the substrate by enzymatic hydrolysis and said leuko color substance is reacted by an oxidation agent to give a colored product and wherein the enzyme substrate is an N— and O— substituted aminophenol derivative of the formula

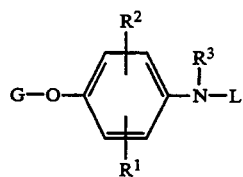

(II)

wherein

G is an organic or inorganic acid residue or a glycoside residue, $R^1$ and $R^2$, which are the same or different, are hydrogen or halogen atoms, SO$_3$H, PO$_3$H$_2$ or a salt of the acid groups, hydroxyl, nitro, carboxyl, carboxamido or cyano groups or alkyl, alkenyl, alkoxy, alkylsulphinyl, alkylsulphonyl, alkoxycarbonyl, alkylcarbonyl, aryl or aralkyl radicals unsubstituted or substituted at least once by hydroxyl, carboxyl, halogen, cyano, SO$_3$H or PO$_3$H$_2$ radicals or a salt of the acid radicals or, when the $R^1$ and $R^2$ substituents are present on neighboring carbon atoms, they form a 1,4-butadiendiyl radical which is unsubstituted or substituted one or more times by SO$_3$H, PO$_3$H$_2$ or a salt of the acid groups, an alkyl or a carboxyl group, $R^3$ is hydrogen or —CO—COOH, SO$_3$H, PO$_3$H$_2$ or a salt of these acid groups, an alkylcarbonyl radical unsubstituted or substituted one or more times by halogen, COOH, SO$_3$H or PO$_3$H$_2$ or a salt of the acid groups or an arylcarbonyl radical unsubstituted or substituted one or more times by SO$_3$H, PO$_3$H$_2$ or a salt of the acid groups, and L is a radical of the formula:

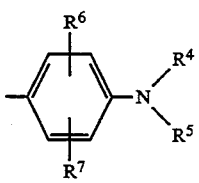

(III)

wherein $R^4$ and $R^5$, which can be the same or different, are alkyl radicals or together represent a saturated C$_3$-C$_6$ hydrocarbon chain which is uninterrupted or interrupted by oxygen, sulphur or nitrogen, wherein the alkyl or the hydrocarbon chain is unsubstituted or substituted one or more times by hydroxyl, carboxyl, alkoxycarbonyl, alkoxy, SO$_3$H$_2$ groups, a salt of one of the acid groups or halogen, and $R^6$ and $R^7$, which can be the same or different, are hydrogen or halogen atoms, hydroxyl or carboxamido groups or alkyl, alkoxy, alkylcarbonyl, alkoxycarbonyl, aryl or aralkyl radicals unsubstituted or substituted by one or more hydroxyl, carboxy, halogen, SO$_3$H or PO$_3$H$_2$ groups or a salt of the acid groups, or L is a pyrazolo-heterocyclic radical of the general formula:

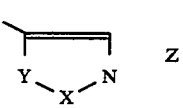

(IV)

wherein

X—Y is —NR$^8$—CO— or —N=CR$^9$, wherein R$^8$ is a hydrogen atom or an alkyl radical and R$^9$ is an alkyl, alkenyl, alkoxy, alkylthio, aryl, aralkyl, each being unsubstituted or substituted by hydroxyl, dialkylphosphinyl, carboxyl, SO$_3$H, PO$_3$H$_2$, a salt of the acid groups or alkoxycarbonyl; or R$^9$ is an amino which is unsubstituted or substituted by one or two alkyl radicals that can be substituted by one or more hydroxyl, carboxyl or alkoxycarbonyl radicals, or when said amino is substituted by two alkyl radicals these radicals can also be joined to form a ring which apart from the first nitrogen atom of the amino group are uninterrupted or interrupted by oxygen, sulphur or a second nitrogen atom or amino is optionally substituted by one or two acyl radicals, alkoxy- or aralkoxycarbonyl radicals, H₂N—CO—, alkyl, aralkyl or arylcarbamoyl radicals; or R⁹ is hydrogen, carboxyl, alkoxycarbonyl, carboxamido or halogen, and Z is —NR¹⁰—N=N—, wherein R¹⁰ is a hydrogen atom or an alkyl or aralkyl radical or Z is an unsaturated chain with 3 to 5 members of nitrogen atoms or carbon atoms or with one or more nitrogen or sulphur atoms, wherein the carbon atoms in the chain are unsubstituted or substituted by alkyl, alkoxy, hydroxyalkyl, alkylthio, hydroxyl, aralkyl, aryl, carboxy, carboxamido, alkoxycarbonyl, cyano, or an amino optionally substituted by one or two alkyl radicals that can be unsubstituted or substituted by one or more hydroxyl, carboxyl or alkoxycarbonyl radicals or halogen, as well as nitrogen atoms, which are not connected via a double bond are unsubstituted or substituted by alkyl or aralkyl or two neighboring chain substituents to form an alkylene radical which alkylene is unsubstituted or substituted or anellated with aryl or a corresponding tautomeric radical of formula II.

2. The hydrolase enzyme substrate of claim 1 wherein the leuko color substance formed therefrom is reacted with an oxidation agent to give a colored product and wherein the oxidation agent is selected from the group consisting of ferricyanide, perborate, iodate and peroxidase/hydrogen peroxide.

3. The enzyme substrate of claim 1, wherein G is a galactoside, glucoside, mannoside, N-acetyl-glucosaminide or an oligosaccharide radical containing 2 to 10 monosaccharide residues.

4. The enzyme substrate of claim 1, wherein G is an N-acetyl-β-D-glucosaminidyl radical.

5. The enzyme substrate of claim 1, wherein G is PO₃MM', SO₃M, a carboxy-attached alkanecarboxylic acid, amino acid or oligopeptide residue and M and M' are hydrogen atoms or alkali metal, alkaline earth metal or ammonium ions.

6. The enzyme substrate of claim 1 wherein the organic acid residue for G is selected from the group consisting of acetic, propionic, butyric, palmitic, stearic, oleic, linoleic, linolenic, glycine, alanine, valine, leucine, isoleucine, phenylalanine and tyrosine.

7. The enzyme substrate of claim 1 wherein aryl is phenyl or naphthyl, aralkyl is benzyl, alkyl is methyl or ethyl, aralkoxy is benzyloxy, alkoxy is methoxy, ethoxy, propoxy, isobutoxy or tert-butoxy, alkenyl is vinyl or allyl, acyl is acetyl, phenacetyl or benzoyl, alkylene is tetramethylene or butadiendiyl and dialkylphosphinyl is dimethylphosphinyl.

8. The enzyme substrate of claim 1 wherein alkyl alone or combined is methyl, ethyl propyl, isobutyl or tert-butyl.

9. The enzyme substrate of claim 1 wherein the enzyme substrate radical L is selected from the group consisting of compounds of the formulas V-XV and XVI as follows:

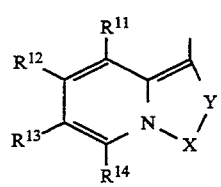
(V)

-continued

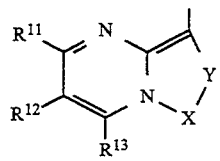
(VI)

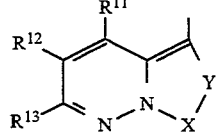
(VII)

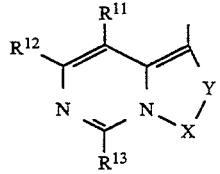
(VIII)

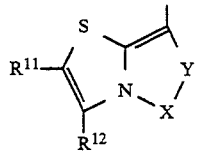
(IX)

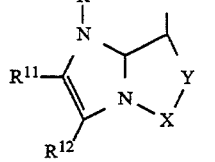
(X)

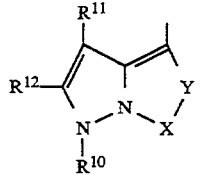
(XI)

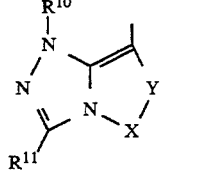
(XII)

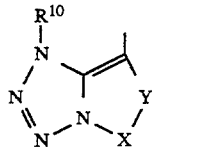
(XIII)

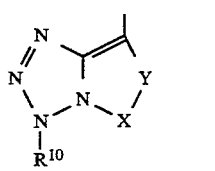
(XIV)

-continued

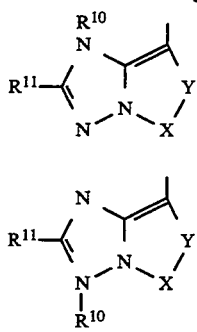
(XV)

(XVI)

and the tautomeric forms thereof.

10. The enzyme substrate of claim 9 wherein L is a radical of the formula V, VI, VII, IX, X, XII and tautomers thereof.

11. The enzyme substrate of claim 1 wherein the enzyme substrate is β-glucosidically-bound N-acetyl-D-glucosaminides of (4-hydroxylphenyl)-2-methyl-pyrazolo[1,5-a]pyridine-3-yl-amine and (4-hydroxyphenyl)-pyrazolo[1,5-a]pyridine-3-yl)-amine.

12. A diagnostic agent for the colorimetric determination of an enzyme comprising an enzyme substrate and an enzyme substrate stabilizer wherein, a leuko colored material is the enzyme substrate and said substrate reacts with an oxidation agent to give a colored product, wherein, the stabilizer of the enzyme substrate is a 1-arylsemicarbazide of the formula:

Ar—NH—NH—CONH$_2$ wherein

Ar is an unsubstituted aryl radical or an aryl substituted by alkyl, alkoxy or halogen and wherein the enzyme substrate is an N- and O-substituted aminophenol derivative of the formula:

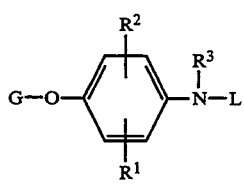
(II)

wherein

G is an organic or inorganic acid residue or a glycoside residue, $R^1$ and $R^2$, which are the same or different, are hydrogen or halogen atoms, SO$_3$H, PO$_3$H$_2$ or a salt of the acid groups, hydroxyl, nitro, carboxyl, carboxamido or cyano groups or alkyl, alkenyl, alkoxy, alkylsulphinyl, alkylsulphonyl, alkoxycarbonyl, alkylcarbonyl, aryl or aralkyl radicals unsubstituted or substituted at least once by hydroxyl, carboxyl, halogen, cyano, SO$_3$H or PO$_3$H$_2$ radicals or a salt of the acid radicals or, when both substituents are present on neighboring carbon atoms, together form a 1,4-butadiendiyl radical which is unsubstituted or substituted one or more times by SO$_3$H, PO$_3$H$_2$ or a salt of the acid groups, an alkyl or a carboxyl group, $R^3$ is hydrogen or —CO—COOH, SO$_3$H, PO$_3$H$_2$ or a salt of these acid groups, an alkylcarbonyl radical unsubstituted or substituted one or more times by halogen, COOH, SO$_3$H or PO$_3$H$_2$ or a salt of the acid groups or an arylcarbonyl radical unsubstituted or substituted one or more times by SO$_3$H, PO$_3$H$_2$ or a salt of the acid groups, and L is a radical of the formula:

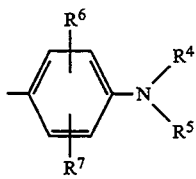
(III)

wherein $R^4$ and $R^5$, which can be the same or different, are alkyl radicals or together represent a saturated $C_3$-$C_6$ hydrocarbon chain which is uninterrupted or interrupted by oxygen, sulphur or nitrogen, wherein the alkyl or the hydrocarbon chain is unsubstituted or substituted one or more times by hydroxyl, carboxyl, alkoxycarbonyl, alkoxy, SO$_3$H groups, a salt of one of the acid groups or halogen, and $R^6$ and $R^7$, which can be the same or different, are hydrogen or halogen atoms, hydroxyl or carboxamido groups or alkyl, alkoxy, alkylcarbonyl, alkoxycarbonyl, aryl or aralkyl radicals unsubstituted or substituted by one or more hydroxyl, carboxy, halogen, SO$_3$H or PO$_3$H$_2$ groups or a salt of the acid groups, or L is a pyrazolo-heterocyclic radical of the general formula:

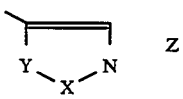
(IV)

wherein

X—Y is —NR$^8$—CO— or —N=CR$^9$, wherein R$^8$ is a hydrogen atom or an alkyl radical and R$^9$ is an alkyl, alkenyl, alkoxy, alkylthio, aryl, aralkyl, each being unsubstituted or substituted by hydroxyl, dialkylphosphinyl, carboxy, SO$_3$H, PO$_3$H$_2$, a salt of the acid groups or alkoxycarbonyl; or an amino which is unsubstituted or substituted by one or two alkyl radicals that can be substituted by one or more hydroxyl, carboxyl or alkoxycarbonyl radicals, wherein, when amino is substituted by two alkyl radicals, these radicals can also be joined to form a ring which, apart from the first nitrogen atom of the amino group, are uninterrupted or interrupted by oxygen, sulphur or a second nitrogen atom or amino is optionally substituted by one or two acyl radicals, alkoxy- or aralkoxycarbonyl radicals, H$_2$N—CO—, alkyl, aralkyl or arylcarbamoyl radicals; or R$^9$ is hydrogen, carboxyl, alkoxycarbonyl, carboxamido or halogen, and Z is —NR$^{10}$—N=N—, wherein R$^{10}$ is a hydrogen atom or an alkyl or aralkyl radical or Z is an unsaturated chain with 3 to 5 members of nitrogen atoms or carbon atoms or with one or more nitrogen or sulphur atoms, wherein the carbon atoms in the chain are unsubstituted or substituted by alkyl, alkoxy, hydroxyalkyl, alkylthio, hydroxyl, aralkyl, aryl, carboxy, carboxamido, alkoxycarbonyl, cyano, amino, which is optionally substituted by one or two alkyl radicals that can be unsubstituted or substituted by one or more hydroxyl, carboxyl or alkoxycarbonyl radicals or halogen, as well as nitrogen atoms, which are not connected via a double bond are unsubstituted or substituted by alkyl or aralkyl or two neighboring chain substituents to form an alkylene radical which alkylene is unsubstituted or substituted or anellated with aryl or a corresponding tautomeric radical of Formula II.

13. The diagnostic agent of claim 12, wherein G is a galactoside, glucoside, mannoside, N-acetyl-glucosaminide or an oligosaccharide radical containing 2 to 10 monosaccharide residues.

14. The diagnostic agent of claim 17, wherein G is an N-acetyl-β-D-glucosaminidyl radical.

15. The diagnostic agent of claim 12, wherein G is PO₃MM', SO₃M, a carboxy-attached alkanecarboxylic acid, amino acid or oligopeptide residue and M and M' are hydrogen atoms or alkali metal, alkaline earth metal or ammonium ions.

16. The diagnostic agent of claim 12 wherein the organic acid residue for G is selected from the group consisting of acetic, propionic, butyric, palmitic, stearic, oleic, linoleic, linolenic, glycine, alanine, valine, leucine, isoleucine, phenylalanine and tyrosine.

17. The diagnostic agent of claim 12 wherein aryl is phenyl or naphthyl, aralkyl is benzyl, alkyl is methyl or ethyl, aralkoxy is benzyloxy, alkoxy is methoxy, ethoxy, propoxy, isobutoxy or tert-butoxy, alkenyl is vinyl or allyl, acyl is acetyl, phenacetyl or benzoyl, alkylene is tetramethylene or butadiendiyl and dialkylphosphinyl is dimethylphosphinyl.

18. The diagnostic agent of claim 12 wherein alkyl alone or combined is methyl ethyl propyl, isobutyl or tert-butyl.

19. The diagnostic agent of claim 12 wherein the enzyme substrate radical L is selected from the group consisting of compounds of the formulas V-XV and XVI as follows:

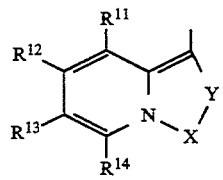 (V)

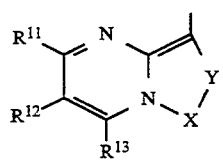 (VI)

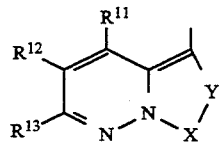 (VII)

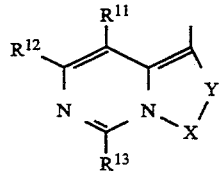 (VIII)

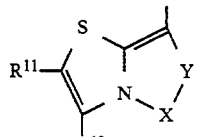 (IX)

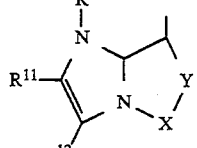 (X)

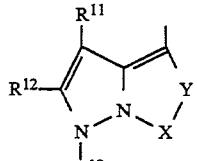 (XI)

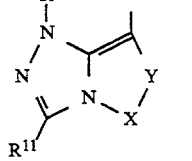 (XII)

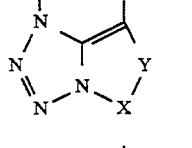 (XIII)

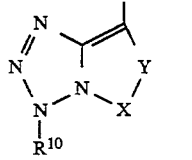 (XIV)

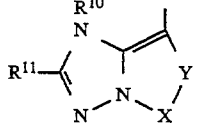 (XV)

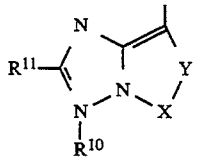 (XVI)

and the tautomeric forms thereof.

20. The diagnostic agent of claim 19 wherein L is a radical of the formula V, VI, VII, IX, X, XII and tautomers thereof.

21. The diagnostic agent of claim 12 wherein the enzyme substrate is β-glucosidically-bound N-acetyl-D-glucosaminides of (4-hydroxylphenyl)-2-methyl-pyrazolo pyridine-3-yl-amine and (4-hydroxyphenyl)-pyrazolo pyridine-3-yl)-amine.

22. The diagnostic agent of claim 12 further comprising an oxidation agent.

23. The diagnostic agent of claim 12 further comprising an oxidation agent.

24. The diagnostic agent of claim 12, comprising the components in carrier-bound form.

* * * * *

UNITED STATES PATENT AND TRADEMARK OFFICE
CERTIFICATE OF CORRECTION

PATENT NO. : 5,391,482
DATED : February 21, 1995
INVENTOR(S) : Dieter Mangold

Page 1 of 5

It is certified that error appears in the above-identified patent and that said Letters Patent is hereby corrected as shown below:

In the cover page, under the section entitled Foreign Application Priority Data, change "3942356" to read as -- P 394235.5 --.

In the cover page, under the section entitled U.S. PATENT DOCUMENT, line 3, change "436/166" to read as -- 435/166 --.

In the cover page, under the section entitled Assistant Examiner, change "Louise D. Leary to read as -- Louise N. Leary.--.

In column 2, line 65, change "stabilizer" to read as -- stabilize --.

In column 5, line 6, change "FIGS." to read -- FIG. --.

In column 6, line 36, change "$SO_3H, PO_3H_2 or$" to read as -- $SO_3H$, $PO_3H$ or --.

In column 6, line 47, change "amd" to read as -- and --.

In column 6, line 65, formula (IV), change " 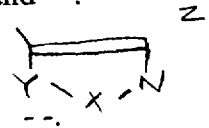 "

to read as --  --.

In column 7, line 5, change "ot" to read as -- of --.

UNITED STATES PATENT AND TRADEMARK OFFICE
CERTIFICATE OF CORRECTION

PATENT NO. : 5,391,482
DATED : February 21, 1995
INVENTOR(S) : Dieter Mangold

It is certified that error appears in the above-identified patent and that said Letters Patent is hereby corrected as shown below:

In column 10, line 47, 1st formula, change "(VI)" to read as -- (V) --.
In column 15, line 15, change "synthesesw" to read as -- synthesis --.
In column 15, formula (IV), change " 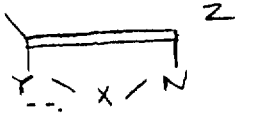 "

to read as --  --

In column 16, delete formula (IV).
In column 17, line 55, delete period in "(i.e. aryl-N=N.)"
to read as -- (i.e. aryl-N=N) --.
In column 18, line 18 change "ar" to read as -- or --.
In column 18, line 19, change "of" to read as -- or --.
In column 18, line 41, change "Keterocycles" to read as -- Heterocycles --.
In column 18, line 41, change "chmistry" to read as -- chemistry --.
In column 18, line 43, change "sons" to read as -- Sons --.

UNITED STATES PATENT AND TRADEMARK OFFICE
CERTIFICATE OF CORRECTION

PATENT NO. : 5,391,482
DATED : February 21, 1995
INVENTOR(S) : Dieter Mangold

It is certified that error appears in the above-identified patent and that said Letters Patent is hereby corrected as shown below:

In column 18, line 67, change "hydrochloride" to read as -- hydrochloric --.
In column 19, line 5, change "hydroclorice" to read as -- hydrochloric --.
In column 20, line 61, change "4-hydroxyphenyl" to read as -- (4-hydroxyphenyl) --.
In column 24, line 4, change "radicals" to read as -- residues --.
In column 24, line 5, change "$R^2$ substituents" to read as -- $R^2$ two substituents --.
In column 24, line 50, formula (IV), change " 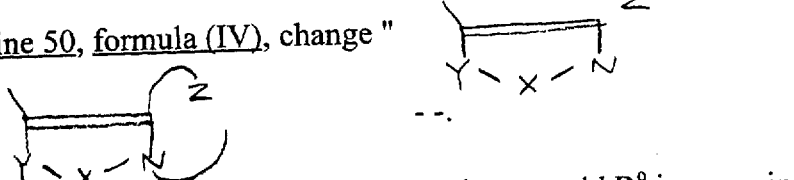 ".
In column 24, line 64, change "said amino" to read as -- said $R^9$ is an amino --.
In column 27, line 16, change "claim 9" to read as -- claim 1 --.
In column 27, line 58, change "radicals or" to read as -- residues or --.
In column 27, line 58, change "acid radicals" to read as -- acid residues --.

UNITED STATES PATENT AND TRADEMARK OFFICE
CERTIFICATE OF CORRECTION

PATENT NO. : 5,391,482
DATED : February 21, 1995
INVENTOR(S) : Dieter Mangold

It is certified that error appears in the above-identified patent and that said Letters Patent is hereby corrected as shown below:

In column 28, line 35, formula (IV), change " 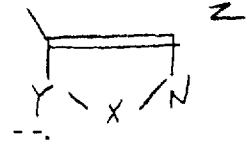 "

to read as --  --.

In column 28, line 44, change "carboxy" to read as -- carboxyl --.
In column 29, line 14, change "claim 17" to read as -- claim 12 --.
In column 30, line 57, change "claim 19" to read as -- claim 12 --.
In column 30, line 62, change "pyrazolo pyridine-3-yl-amine" to read as -- pyrazolo [1,5-a] pyridine-3-yl-amine --.

UNITED STATES PATENT AND TRADEMARK OFFICE
CERTIFICATE OF CORRECTION

PATENT NO. : 5,391,482
DATED : February 21, 1995
INVENTOR(S) : Dieter Mangold

It is certified that error appears in the above-identified patent and that said Letters Patent is hereby corrected as shown below:

In column 30, line 63, change "pyrazolo pyridine-3-yl-amine" to read as -- pyrazolo [1,5-a] pyridine-3-yl-amine --.

Signed and Sealed this

Sixth Day of March, 2001

Attest:

NICHOLAS P. GODICI

Attesting Officer     Acting Director of the United States Patent and Trademark Office